United States Patent [19]

Samaan et al.

[11] Patent Number: 4,600,783

[45] Date of Patent: Jul. 15, 1986

[54] PROCESS FOR PREPARING ACEMETACIN

[75] Inventors: Samir Samaan; Harald Horstmann, both of Wuppertal, Fed. Rep. of Germany

[73] Assignee: Bayer Aktiengesellschaft, Leverkusen, Fed. Rep. of Germany

[21] Appl. No.: 726,880

[22] Filed: Apr. 25, 1985

[30] Foreign Application Priority Data

May 8, 1984 [DE] Fed. Rep. of Germany ....... 3416895

[51] Int. Cl.⁴ .......................................... C07D 209/28
[52] U.S. Cl. .................................................... 548/501
[58] Field of Search ......................................... 548/501

[56] References Cited

U.S. PATENT DOCUMENTS 4,104,278  8/1978  Boltze et al. .................... 548/501
4,165,428  8/1979  Noda et al. ...................... 548/501

Primary Examiner—Glennon H. Hollrah
Assistant Examiner—D. B. Springer
Attorney, Agent, or Firm—Sprung, Horn, Kramer & Woods

[57] ABSTRACT

Acemetacin is prepared by reaction of an indometacin with tert.-butyl halogenoacetate and subsequent cleavage with sulphuric acid and/or sulphonic acid.

7 Claims, No Drawings

PROCESS FOR PREPARING ACEMETACIN

The invention relates to a process for preparing acemetacin.

A process for preparing acemetacin of the formula

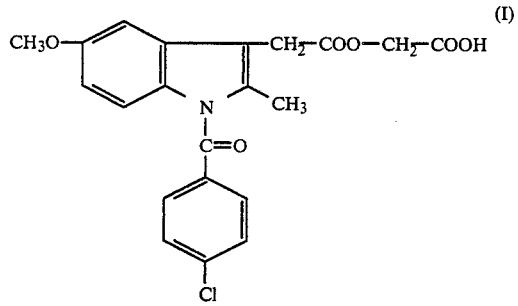

is described for example in Application Ser. No. 463,370, filed Feb. 3, 1983, now pending corresponding to German Published Specification DE-OS No. 3,206,885. However, the technical implication of the process is not without problems.

A new process has been found for preparing acemetacin, characterized in that indometacins of the general formula II

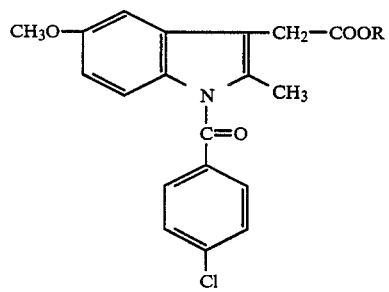

in which
R stands for alkali metal or alkali earth metal or for the group $MY_4$
in which
M stands for nitrogen or phosphorus and
Y has the meaning hydrogen, identical or different, optionally substituted alkyl, cycloalkyl or aryl,
are reacted with tert.-butyl halogenoacetate of the general formula III $$Hal-CH_2-COO-C(CH_3)_3 \quad (III)$$

in which Hal stands for chlorine, bromine or iodine, within the temperature range from $-30°$ C. to $+70°$ C. in the presence of inert organic solvents or mixtures thereof, and subsequently the further reaction is carried out within the temperature range from $-30°$ to $+120°$ C. with sulphuric acid and/or sulphonic acids.

The process according to the invention is a particularly advantageous way of preparing acemetacin.

Indometacins for the process according to the invention are known per se.

The first part of the reaction according to the invention is generally carried out within the temperature range from $-30°$ to $+70°$ C., preferably 0° to 60° C.

Sulphonic acids can be for example methanesulphonic acids or p-toluenesulphonic acid.

It is of course also possible to use mixtures of sulphuric acids and the sulphonic acids.

The sulphuric acids and/or the sulphonic acids can be used in catalytic amounts to about equimolar amounts. It is preferable to use 1 to 50% of the molar amount.

The starting compounds for the process according to the invention (formula II and III) are generally used in approximately equimolar amounts.

Suitable solvents for the reaction according to the invention are polar and aprotic solvents, such as chloroform, dichloromethane, toluene, acetone, butan-2-one and methyl isobutyl ketone. For the cleavage reaction as acetic acid can be used as solvents. Preferred solvents are acetone and acetic acid and toluene. Particularly preferred solvents for ester formation are butan-2-one, acetone and methyl isobutyl ketone. The compounds of the general formula II are preferably in the form of potassium, sodium, quaternary ammonium or phosphonium salts.

In a preferred embodiment of the process according to the invention, the first stage is carried out in the presence of a phase transfer catalyst. Preferred phase transfer catalysts for the process according to the invention are ammonium salts and/or phosphonium salts.

Particularly preferred phase transfer catalysts are: benzyltriethylammonium chloride, tetrabutylammonium bromide, tetrabutylammonium hydrogensulphate, methyltrioctylammonium chloride, tetrabutylphosphonium bromide and hexadecyltributylphosphonium bromide.

The process according to the invention can be carried out in two stages or as a single-vessel process, that is to say without isolation of the intermediate product. The process according to the invention is particularly preferably carried out without isolation of the intermediate product.

If, for example, the reaction according to the invention is carried out in acetone as the solvent and in the presence of benzyltriethylammonium chloride as the phase transfer catalyst (PTC), the process can be represented by the following diagram:

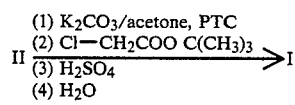

In this version the intermediate product is not isolated. If it is desired to isolate the tert.-butyl ester of acemetacin, water is added in place of the acid, thereby crystallising out the ester in high purity and 95% yield.

It is known that tert.-butyl esters can be selectively cleaved with trifluoroacetic acid or formic acid (cf. for example: T. W. Greene, Protective Groups in Organic Synthesis, Wiley & Sons, New York 1981, pp. 168). However, these reagents are relatively costly and if they are to be handled on an industrial scale require special safety measures. The use of aqueous mineral acids such as hydrochloric acid, hydrobromic acid or sulphuric acid for cleaving the tert.-butyl ester of acemetacin to obtain acemetacin with high selectivity has been found to be unsuitable. Either the ester is stable (for example at 25°-30° C. in 50% strength sulphuric acid) or the cleavage is aselective, i.e. up to 60% of the product is the starting compound indometacin.

According to the invention, it is surprisingly possible to cleave the tert.-butyl ester of acemetacin with catalytic amounts of concentrated sulphuric acid or sulphonic acids (96-98% strength) to obtain acemetacin in high yield and purity. The process according to the invention has the particular advantage that the reaction products are simple to work up, namely by addition of water to crystallize out the acemetacin, which is then filtered off.

Acemetacin is a known antiinflammatory agent in human and veterinary medicine.

EXAMPLE 1 (TERT.-BUTYL ESTER OF ACEMETACIN)

50.0 g of indometacin and 20.0 g of potassium carbonate are stirred at 56° C. in 280 ml of acetone for 30 minutes. The mixture is cooled down to 40° C., 1.0 g of benzyltriethylammonium chloride is added, and 25.3 g of tert.-butyl chloroacetate are added dropwise in the course of 30 minutes. Stirring is continued at 40° C. until the reaction has ended (5 to 6 hours, monitoring by thin layer chromatography). After the reaction has ended, the mixture is cooled down to 20° C. and is poured onto 1 liter of water. The solids are filtered off with suction, are thoroughly washed with water and are dried at 50° C. in vacuo.

Yield: 63.6 g=96% of theory
Melting point: 100° to 101° C.
Purity by HPLC: 98.1%.

EXAMPLE 2 (ACEMETACIN)

10 g of the tert.-butyl ester of acemetacin in according to example 1 in 80 ml of toluene are treated at 45° C. with 0.4 ml of methanesulphonic acid, and the mixture is stirred at said temperature for 4 hours. A further 0.2 ml of methane-sulphonic acid is added, and the mixture is stirred at 45° C. for a further 4 hours. It is cooled down and n-hexane is added to precipitate the product. The solids are filtered off with suction, and washed with water, are dried and are recrystallized once more from toluene n-hexane.

Yield: 7.9 g=89.7% of theory.

EXAMPLE 3 (ACEMETACIN SINGLE-DROP PROCESS)

25 g of indometacin, 10 g of potassium carbonate and 190 ml of acetone are stirred at 56° C. for 30 minutes. The mixture is cooled down to 40° C., 0.5 g of benzyltriethylammonium chloride is added, and 15.6 g of tert.-butyl chloroacetate are added dropwise. After 5 hours at 40° C. the reaction is complete (monitored by thin layer chromatography). The mixture is cooled down to 10° C. and 20 ml of concentrated sulphuric acid are then added dropwise in such a way that the temperature does not exceed 25° C. The mixture is stirred at 20° and 25° C. for 6 hours (monitored by thin layer chromatography), about 500 ml of water are added, and the solids are filtered off with suction, are dried in vacuo and are recrystallized from acetone-water.

Yield: 26.7 g=91.9% of theory.

EXAMPLE 4 (ACEMETACIN)

15.0 g of the tert.-butyl ester of acemetacin according to example 1 are suspended at 20-25 °D in 90 ml of glacial acetic acid, and 1.5 ml of concentrated sulphuric acid are added. After about 30 minutes a clear solution forms After a further 30 minutes acemetacin begins to crystallise out. Stirring is continued for a total of 6 hours until the cleavage is complete (monitored by thin layer chromatography). 100 ml of water are added, and the solids are filtered off with suction, are washed thoroughly with water and are dried at 50° C. in vacuo.

Yield: 13.2 g (95.2% of theory).

EXAMPLE 5 (ACEMETACIN)

0.4 g of p-toluenesulphonic acid is added to 9.6 g of tert.-butyl ester of acemetacin according to example 1 in 30 ml of acetic acid, and the mixture is stirred at 100° C. for 4 to 5 hours. After the mixture has cooled down to room temperature, 50 ml of water are added. Acemetacin precipitates, is filtered off with suction and is recrystallized from acetone/water.

Yield: 8.0 g=90.6% of theory of pure product.

It will be understood that the specification and examples are illustrative but not limitative of the present invention and that other embodiments within the spirit and scope of the invention will suggest themselves to those skilled in the art.

We claim:

1. A process for preparing acemetacin, comprising in a first step reacting indometacin of the formula

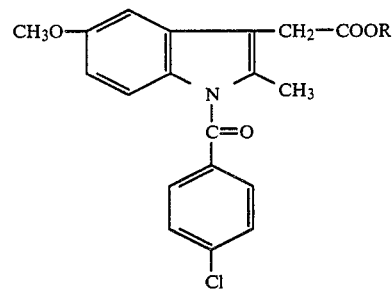

in which
R is an alkali metal or alkaline earth metal or the group MY₄,
M is nitrogen or phosphorus, and
Y each independently is hydrogen, or an optionally substituted alkyl, cycloalkyl or aryl,
with a tert.-butyl halogenoacetate of the formula

in which
Hal is chlorine, bromine or iodine, within the temperature range from −30° C. to +70° C. in the presence of at least one inert organic solvent and a phase transfer catalyst, and subsequently in a second step completing reaction within the temperature range from −30° C. to +120° C. in the presence of sulphuric acid and/or sulphonic acid.

2. A process according to claim 1, wherein both steps of the reaction are carried out successively in the same vessel without intermediate isolation.

3. A process according to claim 9, wherein the first step of the reaction is carried out in an organic solvent in the presence of an ammonium salt phase transfer catalyst.

4. A process according to claim 1, wherein the phase transfer catalyst is benzyltriethylammonium chloride.

5. A process according to claim 1, wherein the product of the first step is the tert.-butyl ester of acemetacin and is isolated as an intermediate product, the second step cleavage being separately carried out.

6. A process according to claim 1, wherein the second step cleavage to give acemetacin is carried out in at least one of glacial acetic acid and acetone in the presence of sulphonic acid in from catalytic up to equimolar amount.

7. A process according to claim 1, wherein the second step cleavage is carried out with p-toluenesulphonic acid in a solvent which contains acetic acid.

* * * * *